US007727770B2

(12) United States Patent
Byrne et al.

(10) Patent No.: US 7,727,770 B2
(45) Date of Patent: Jun. 1, 2010

(54) SYSTEM AND METHOD FOR SPECTROPHOTOMETRIC MEASUREMENT OF TOTAL ALKALINITY USING A LIQUID CORE WAVEGUIDE

(75) Inventors: Robert H. Byrne, St. Petersburg, FL (US); Eric Kaltenbacher, St. Petersburg, FL (US); Xuewu Liu, St. Petersburg, FL (US)

(73) Assignee: University of South Florida, Tampa, FL (US)

( * ) Notice: Subject to any disclaimer, the term of this patent is extended or adjusted under 35 U.S.C. 154(b) by 1014 days.

(21) Appl. No.: 11/279,971

(22) Filed: Apr. 17, 2006

(65) Prior Publication Data

US 2006/0234389 A1    Oct. 19, 2006

Related U.S. Application Data

(60) Provisional application No. 60/672,474, filed on Apr. 18, 2005.

(51) Int. Cl.
*G01N 21/64* (2006.01)
(52) U.S. Cl. ........................ 436/163; 436/171
(58) Field of Classification Search ................ 436/133, 436/163, 172
See application file for complete search history.

(56) References Cited

U.S. PATENT DOCUMENTS 4,209,299 A * 6/1980 Carlson ...................... 436/150
4,318,709 A * 3/1982 Falb et al. ................... 436/163
4,526,755 A * 7/1985 Vincent et al. ............... 422/90
5,416,879 A * 5/1995 Liu .............................. 385/125
5,660,790 A * 8/1997 Lawrence et al. ........... 422/56
6,436,717 B1 * 8/2002 Wu ............................. 436/133

OTHER PUBLICATIONS

Michael D. Degrandpre et al., Calibration-Free Optical Chemical Sensor, Analytical Chemistry, vol. 71, No. 6, Mar. 15, 1999, p. 1152-1159.
Eric Kaltenbacher et al., A Compact, In-situ, Spectrophotometric Sensor for Aqueous Environments: Design and Applications, p. 41-45.
Frank J. Millero, Thermodynamics of the Carbon Dioxide System in the Oceans, Geochimica et Cosmochimica Acta, vol. 59, No. 4, p. 661-677, 1995.
Gillian L. Robert-Baldo, Spectrophotometric Determination of Seawater pH Using Phenol Red, Analytical Chemistry, vol. 57, No. 13, Nov. 1985, p. 2564-2567.
R.F. Weiss, Carbon Dioxide in Water and Seawater: The Solubility of a Non-Ideal Gas, Marine Chemistry, vol. 2, 1974, p. 203-215.

(Continued)

*Primary Examiner*—Robert J Hill, Jr.
*Assistant Examiner*—Dwan A Gerido
(74) *Attorney, Agent, or Firm*—Thomas E. Toner; Smith & Hopen, P.A.

(57) ABSTRACT

A system and method for spectrophotometrically measuring the total alkalinity of a liquid sample. In a particular aspect, the method involves equilibration of a $CO_2$ gas with a sample solution across the permeable walls of a Teflon AF 2400 liquid core waveguide. The waveguide acts as both an equilibration membrane and an optical cell in which spectrophotometric pH measurements are obtained via measurements of absorbance ratios.

18 Claims, 5 Drawing Sheets

OTHER PUBLICATIONS

Wensheng Yao et al., Simplified Seawater Alkalinity Analysis: Use of Linear Array Spectrometers, Deep Sea Research I, vol. 45, 1998, p. 1383-1392.

Wensheng Yao et al., Spectrophotometric Determination of Freshwater pH Using Bromocresol purple and Phenol Red, Environmental Science & Technology, 2001, vol. 35, p. 1197-1201.

S. McElligott et al., Discrete Water Column Measurements of CO2 Fugacity and pHT in Seawater: A Comparison of Direct Measurements and Thermodynamic Calculations, Marine Chemistry 60, 1998, p. 63-73.

Ingo Pinnau et al., Gas and Vapor Transport Properties of Amorphous Perfluorinated Copolymer Membranes Based on 2,2-Bistrifluoromethyl-4,5-Difluoro-1,3Dioxole/Tetrafluoroethylene, Journal of Membrane Science 109, 1996, p. 125-133.

Robert D. Waterbury et al., Long Pathlength Absorbance Spectroscopy: Trace Analysis of Fe(II) Using a 4.5 M Liquid Core Waveguide, Analytica Chimica Acta 357, 1997, p. 99-102.

A. Yu. Alentiev et al., High Transport Parameters and Free Volume of Perfluorodioxole Copolymers, Journal of Membrane Science 126, 1997, p. 123-132.

Tonya D. Clayton et al., Spectrophotometric Seawater pH Measurements: Total Hydrogen Ion Concentration Scale Calibration of M-Cresol Purple and At-Sea Results, Deep Sea Research I, vol. 40, No. 10, 1993, p. 2115-2129.

Robert H. Byrne, Standardization of Standard Buffers by Visible Spectrometry, Analytical Chemistry, vol. 59, 1987, p. 1479-1481.

Robert H. Byrne et al., High Precision Multiwavelength pH Determinations in Seawater Using Cresol Red, Deep-Sea Reserch, vol. 36, No. 5, 1989, p. 803-810.

Robert H. Byrne et al., Construction of a Compact Spectrofluorometer /Spectrophotometer System Using a Flexible Liquid Core Waveguide, Talanta 50, 2000, p. 1307-1312.

Amanda E. Hopkins, In-Situ Spectrophotometric pH Measurements: the Effect of Pressure of Thymol Blue Protonation and Absorbance Characteristics, Marine Chemistry 71, 2000, p. 103-109.

Wensheng Yao et al., Determination of Nanomolar Concentration of Nitrite and Nitrate in Natural Waters Using Long Path Length Absorbance Spectroscopy, Environmental Science & Technology, vol. 32, No. 17, 1998, p. 2646-2649.

Robert H. Byrne et al., Autonomous In-Situ Analysis of the Upper Ocean, Sea Technology.

Eric A. Kaltenbacer et al., Design and Application of a Chemical Sensor Compatible with Autonomous Ocean-Sampling Networks, IEEE Journal of Oceanic Engineering, vol. 26, No. 4, Oct. 2001, p. 667-670.

Wensheng Yao et al., Determination of Trace Chromium(VI) and Molybdenum(VI) in Natural and Bottled Mineral Waters Using Long Pathlength Absorbance Spectroscopy (LPAS), Talanta 48, 1999, p. 277-282.

Robert H. Byrne et al., Use of Liquid Core Waveguides for Long Pathlength Absorbance Spectroscopy: Principles and Practice, Limnol. Oceanogr., 46(3), 2001, p. 740-742.

Michael R. Callahan et al., In-Situ Measurements of Cu in an Estuarine Environment Using a Portable Spectrophotometric Analysis System, Environmental Science & Technology, vol. 38, No. 2, 2004, p. 587-593.

Michael R. Callahan et al., Long Pathlength Absorbance Spectroscopy: Trace Copper Analysis Using a 4.4M Liquid Core Waveguide, Talanta 58, 2002, p. 891-898.

Robert H. Byrne et al., Spectrophotometric Measurement of Total Inorganic Carbon in Aqueous Solutions Using a Liquid Core Waveguide, Analytica Chimica Acta 451, 2002, p. 221-229.

Wensheng Yao et al., Spectrophotometric Determination of Freshwater pH Using Bromocresol Purple and Phenol Red, Environmental Science & Technology, vol. 35, 2001, p. 1197-1201.

Robert H. Byrne et al., The Role of pHT Measurements in Marine CO2-System Characterizations, Deep-Sea ResearchI, vol. 46, 1999, p. 1985-1997.

* cited by examiner

Fig. 5

Calibration of Constant C in Eq. 14 using CRM with TA = 0.00226986 μmol kg$^{-1}$

| A 589 | A 432 | R | logR terms | pH | log(TA+[H+] | C |
|---|---|---|---|---|---|---|
| 0.28036 | 0.38085 | 0.73614 | -0.58789 | 5.23132 | -2.64288 | 0.05449 |
| 0.27952 | 0.37928 | 0.73698 | -0.58739 | 5.23182 | -2.64288 | 0.05399 |
| 0.27060 | 0.36671 | 0.73791 | -0.58683 | 5.23238 | -2.64288 | 0.05342 |
| 0.27050 | 0.36632 | 0.73843 | -0.58653 | 5.23268 | -2.64288 | 0.05311 |
| 0.27690 | 0.37570 | 0.73702 | -0.58737 | 5.23184 | -2.64288 | 0.05396 |
| 0.32136 | 0.43625 | 0.73664 | -0.58759 | 5.23162 | -2.64288 | 0.05419 |
| 0.31905 | 0.43344 | 0.73609 | -0.58793 | 5.23128 | -2.64288 | 0.05452 |
| 0.31962 | 0.43440 | 0.73577 | -0.58812 | 5.23109 | -2.64288 | 0.05471 |
| 0.31874 | 0.43250 | 0.73697 | -0.58740 | 5.23181 | -2.64288 | 0.05399 |
| Average | | 0.73688 | -0.58745 | 5.23176 | -2.64288 | 0.05404 |
| *Constant Calculations* | | | | | | |
| S=34.217 | T=298.15 | | | | | |
| | | | | | | |
| log$K_0$ | | -1.545037054 | | | | |
| log$K_1$ | | -5.858746183 | | | | |
| log$K_I$ | | -5.81718993 | | | | |
| | | | | | | |
| log($K_0K_1/K_I$) | | -1.586593307 | | | | |
| log($K_0K_1pCO_2/K_I$) | | -2.109472053 | | | | |

SYSTEM AND METHOD FOR SPECTROPHOTOMETRIC MEASUREMENT OF TOTAL ALKALINITY USING A LIQUID CORE WAVEGUIDE

CROSS REFERENCE TO RELATED APPLICATIONS

This application claims priority to currently pending U.S. Provisional Patent Application No. 60/672,474, entitled, "Alkalinity Sensor", filed Apr. 18, 2005.

BACKGROUND OF INVENTION

Seawater alkalinity ($A_T$), defined as a difference between the excess concentrations of proton acceptors over proton donors in 1 kg of seawater, is one of the important parameters in carbon dioxide systems. Due to its invariance during $CO_2$ gas exchange and biological activity, $A_T$ is considered to be a cornerstone in analytical assessments of oceanic $CO_2$ cycling. Anomalies of $A_T$ normalized to salinity have been contributed to water mass movement and/or dissolution of calcium carbonate.

Conventional systems and method for measuring seawater $A_T$ usually involve acid titration of the bases to carbonic acid end point by either a single step addition or sequential stepwise addition. The multi-step titration method is widely used on shipboard measurements due to its high precision and automated operation. The combined speed and simplicity of single-step titration with spectrophotometric pH determinations for measurement of end point excess acid has been shown. Such methods have greatly improved the precision of alkalinity measurements. However, these end point detections require accurate knowledge of end point pH without the influence of $CO_2$ generated in titration steps and thus usually involve a purge step. Such step makes the automation of an online instrument difficult. The multipoint volumetric titration remains the standard procedure for discrete sampling.

Accordingly, what is needed in the art is an improved system and method for measuring the total alkalinity of a sample liquid which overcomes the limitations of the prior art systems.

SUMMARY OF INVENTION

In accordance with the present invention, a method for measuring the total alkalinity of a sample liquid using a liquid core waveguide having a gas permeable membrane and an equilibration cell is provided. In accordance with the method of the present invention, the liquid core waveguide is positioned in an interior cavity of an equilibration chamber. A flow of gas is then introduced into the interior cavity of the equilibration chamber. The sample liquid is treated with a pH indicator and introduced into the interior of the liquid core waveguide. The interior of the liquid core waveguide is then sealed and the gas is allowed to equilibrate across the gas permeable membrane of the liquid core waveguide. After equilibration is obtained, the absorbance ratio of the sample liquid is measured at a plurality of wavelengths using the liquid core waveguide. The total alkalinity ($A_T$) of the sample liquid is then calculated from the measured absorbance ratios, according to the equation:

$$\log(A_T+[H^+])=\log(K_1'(K_0)_i(pCO_2)/K_1)+ E+\log((R(25)-e_1)(e_2-R(25)e_3))$$

where;

$[H^+]=10^{-pH}$, $K_0$ is the Henry's law constant, $K_1'$ is the dissociation constant of carbonic acid, the subscript i refers to the sample liquid within the waveguide, E is an empirical derived constant, $K_1$ is an indicator dye dissociation constant, $R(25)$ is a ratio of the pH indicator absorbance at 589 and 432 nm, and $e_1$ and $e_2$ and $e_3$ are molar absorptivity ratios appropriate to the pH indicator.

In one embodiment, the pH indicator is a sulfonephthalein pH indicator, such as bromocresol purple.

Additionally, the method of the present invention may include passing the flow of gas though a thermostated water bath prior to introducing the flow of gas into the interior cavity of the equilibration chamber. The equilibration chamber may further be housed in a thermostated water bath.

To establish a reference point for the absorbance ratio measurements, the absorbance ratio of the liquid sample without the pH indicator is measured.

The gas is introduced at a controlled rate into the interior of the equilibration chamber. The gas may be any of a variety of gases, but more specifically the gas is $CO_2$ or $NaHCO_3$. In a specific embodiment, the gas is 30% $CO_2$.

Liquid core waveguides (LCW) constrain light propagation within a liquid medium when the liquid has a higher index of refraction (RI) than the surrounding tubing of the LCW. In a particular embodiment of the invention, the liquid core waveguide is a Teflon AF 2400 liquid core waveguide.

According to the present invention, a system for measuring the total alkalinity of a sample liquid is provided. In one embodiment, the system includes an equilibration chamber having an interior cavity and a liquid core waveguide having a gas permeable membrane. A gas supply is provided to supply gas to the interior cavity of the equilibration chamber and a sample liquid supply is provided to supply a sample liquid including a pH indicator into the interior of the liquid core waveguide. The liquid core waveguide is positioned within the interior cavity of the equilibration chamber and the liquid core waveguide is used to measure the absorbance ratio of the sample liquid at a plurality of wavelengths. Means are also provided for calculating the total alkalinity ($A_T$) of the sample liquid from the measured absorbance ratios according to the equation:

$$\log(A_T+[H^+])=\log(K_1'(K_0)_i(pCO_2)/K_1)+ E+\log((R(25)-e_1)(e_2-R(25)e_3))$$

where;

$[H^+]=10^{-pH}$, $K_0$ is the Henry's law constant, $K_1'$ is the dissociation constant of carbonic acid, the subscript i refers to the sample liquid within the waveguide, E is an empirical derived constant, $K_1$ is an indicator dye dissociation constant, $R(25)$ is a ratio of the pH indicator absorbance at 589 and 432 nm, and $e_1$ and $e_2$ and $e_3$ are molar absorptivity ratios appropriate to the pH indicator.

Accordingly, the present invention provides a novel $A_T$ methodology involving spectrophotometric pH measurements with Liquid Core Waveguide techniques. Liquid core waveguides (LCW) constrain light propagation within a liquid medium when the liquid has a higher index of refraction (RI) than the surrounding tubing of the LCW. The procedure of the present invention obviates the use of strong acids in volumetric titration, provides rapid sample throughput using very small samples, and achieves measurement precisions comparable to multipoint titrations. Additionally, the method is amenable to autonomous operation and in-situ analysis of the surface ocean.

BRIEF DESCRIPTION OF THE DRAWINGS

For a fuller understanding of the invention, reference should be made to the following detailed description, taken in connection with the accompanying drawings, in which:

FIG. 5 includes a table which illustrates the constant E in Eq. 14 as measured with certified reference material (CRM) provided by Dr. Andrew Dickson with known $A_T$.

DETAILED DESCRIPTION OF THE PREFERRED EMBODIMENT

Figure 1:
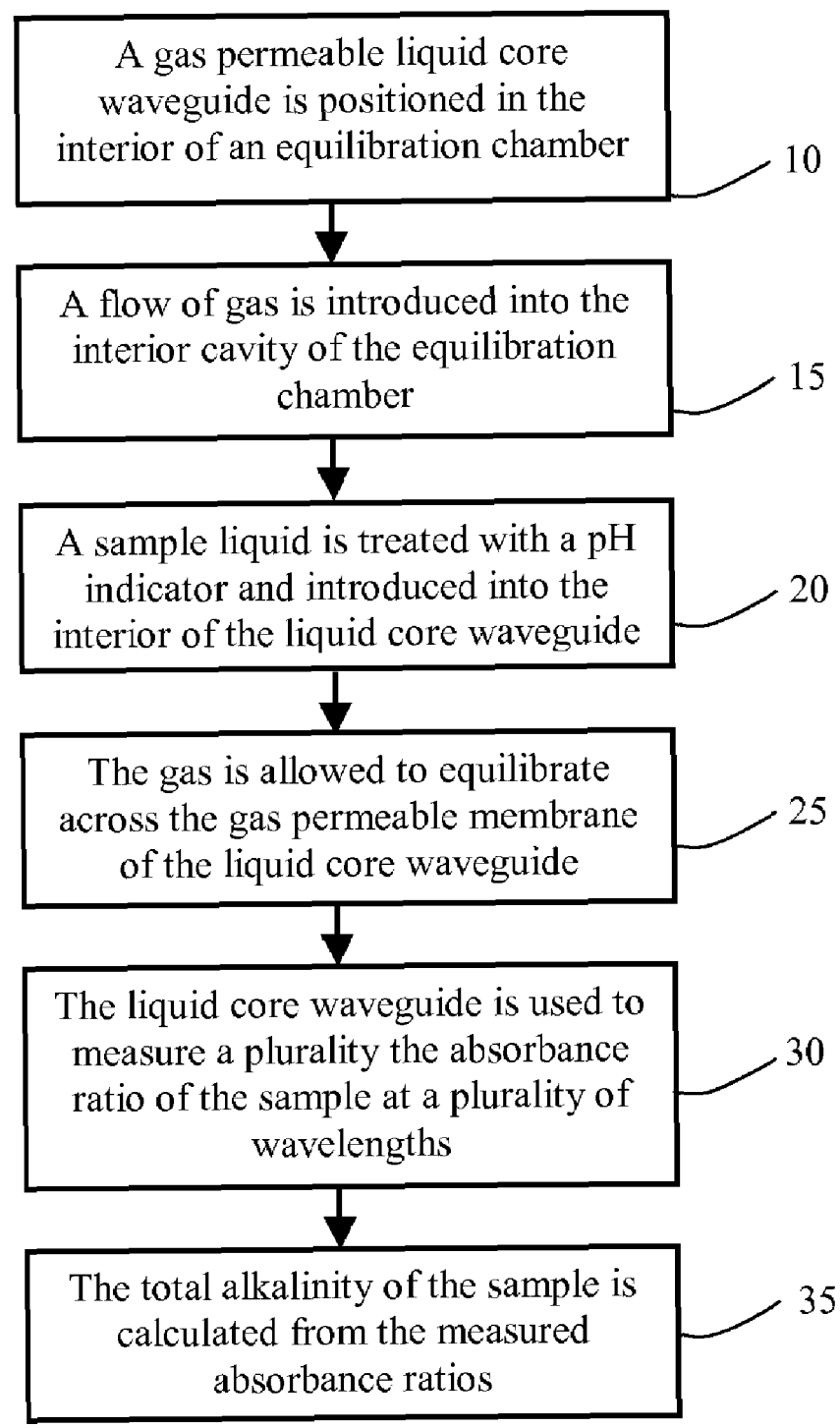
FIG. 1 is flow diagram illustrating a method in accordance with an embodiment of the invention.

FIG. 1 is a flow diagram illustrating a method for measuring total alkalinity in accordance with the present invention. In accordance with the present invention, a method for measuring the total alkalinity of a sample liquid using a liquid core waveguide having a gas permeable membrane and an equilibration chamber is provided. The liquid core waveguide is positioned within the interior cavity of the equilibration chamber 10. A flow of gas is introduced into the interior cavity of the equilibration chamber 15, such that the gas surrounds the liquid core waveguide positioned within the chamber. The sample liquid is treated with a pH indicator and then introduced into the interior of the liquid core waveguide 20. The interior of the liquid core waveguide is then sealed and the gas is allowed to equilibrate across the gas permeable membrane of the liquid core waveguide 25. After equilibration is obtained, the absorbance ratio of the sample liquid is measured at a plurality of wavelengths using the liquid core waveguide 30. The total alkalinity ($A_T$) of the sample liquid is then calculated from the measured absorbance ratios 35, according to the equation:

$$\log(A_T+[H^+])=\log(K_1'(K_0)_i(pCO_2)/K_1)+E+\log((R(25)-e_1)(e_2-R(25)e_3))$$

where;

$[H^+]=10^{-pH}$, $K_0$ is the Henry's law constant, $K_1'$ is the dissociation constant of carbonic acid, the subscript i refers to the sample liquid within the waveguide, E is an empirical derived constant, $K_1$ is an indicator dye dissociation constant, R(25) is a ratio of the pH indicator absorbance at 589 and 432 nm, and $e_1$ and $e_2$ and $e_3$ are molar absorptivity ratios appropriate to the pH indicator.

In accordance with one embodiment of the present invention, pH measurements within a Teflon AF 2400 liquid core waveguide are used for robust measurements of total alkalinity ($A_T$). Teflon AF 2400 liquid core waveguides are well suited to $CO_2$ system measurements due to high gas permeability coefficients of Teflon AF 2400, and the simplicity of measurements in which Teflon AF 2400 serves as both the optical cell and $CO_2$ equilibration membrane.

Figure 2:
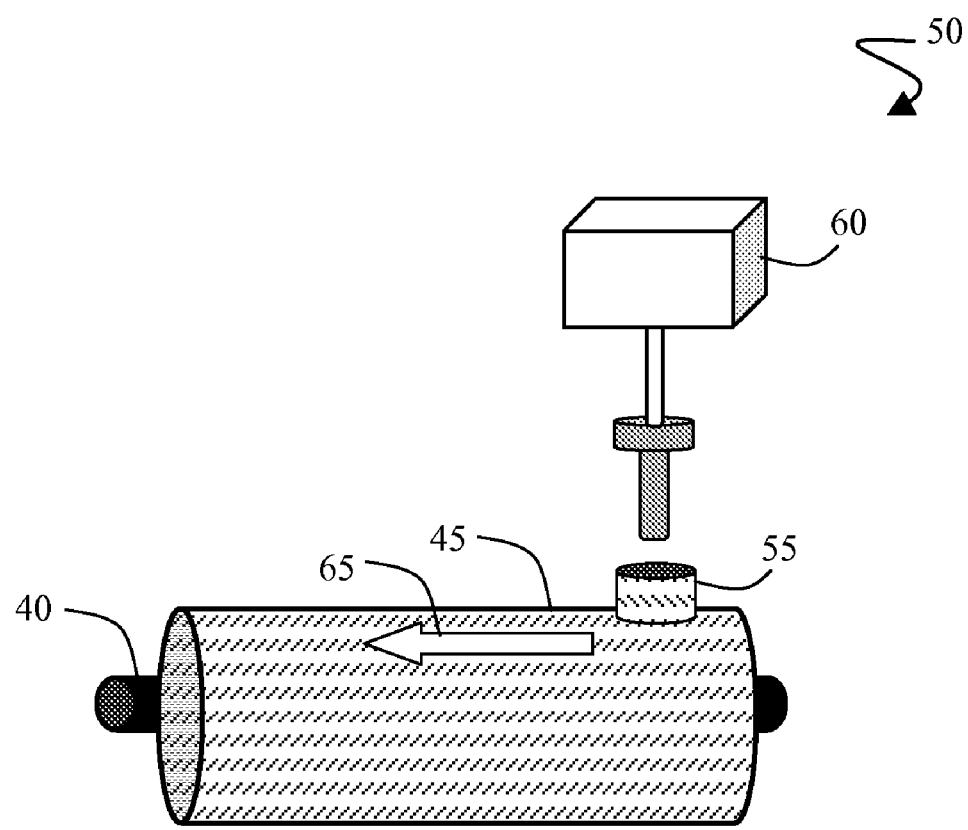
FIG. 2 is an illustration of an embodiment of the system configuration used for spectrophotometric measurements of total alkalinity in accordance with the present invention.

FIG. 2 an embodiment of the system 50 used for spectrophotometric measurements of total alkalinity in accordance with the present invention. The solution within the liquid crystal waveguide 40 contains a sulfonephthalein pH indicator and seawater as the sample to be measured. In one embodiment, the pH indicator is about 2 μM. In a specific embodiment, the outer solution within the cavity of the equilibration chamber 45 and surrounding the waveguide 40 is a $CO_2$ gas mixture (30% $CO_2$). Upon equilibration, the pH of the inner sample solution becomes constant. Since the fugacity of the $CO_2$ ($fCO_2$) of the inner and outer solutions are identical at equilibrium, the total alkalinity of samples inside of the LCW can then be calculated from known thermodynamic relationships.

The alkalinity of seawater is defined as:

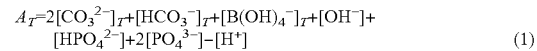

$$A_T=2[CO_3^{2-}]_T+[HCO_3^-]_T+[B(OH)_4^-]_T+[OH^-]+[HPO_4^{2-}]+2[PO_4^{3-}]-[H^+] \quad (1)$$

In one embodiment utilizing 30% of $CO_2$ as equilibration gas, the pH upon equilibration is below 5.7 over a wide range of $A_T$ normally encountered in natural waters. Under this condition, all other species X ($=[CO_3^{2-}]_T$, $[B(OH)_4^-]_T$, ...) are converted to protonated species and equal amount of $HCO_3^-$ is formed according to this reaction:

$$CO_2*+H2O+X^-=HCO_3^-+HX \quad (2)$$

The only important species is $[HCO_3^-]_T$ and $[H^+]$ between pH 5 to 6.

The dissociation constant of carbonic acid is expressed in terms of the concentrations ([]) of $H^+$, $HCO_3^-$ and $CO_2*$ as $$K_1'=[H^+][HCO_3^-]_T/[CO_2*] \quad (3)$$

where $[CO_2*]$ is the sum solution concentration of $CO_2$ and $H_2CO_3$ ($[CO_2*]=[CO_2]+[H_2CO_3]$). $[CO_2*]$ can also be expressed in terms of the Henry's law constant ($K_0$) and the fugacity of $CO_2$ (i.e. $fCO_2$) in solution:

$$[CO_2*]=K_0 fCO_2. \quad (4)$$

Combining Eqs. (1) and (2), the $[HCO_3^-]$ of the solution inside a liquid core waveguide is given as,

$$[HCO_3^-]_i=K_1'(K_0)_i(fCO_2)_i/[H^+]i \quad (5)$$

where the subscript "i" refers to the solution inside the LCW.

As such, for an equilibrated sample (pH<5.5 for $A_T$ is about 2000 μmol/kg and 30% $CO_2$ as equilibrating gas), Eq. (4) could be simplified to:

$$A_T=[HCO_3^-]-[H^+] \quad (6)$$

Thus the seawater alkalinity can be conveniently obtained by measurement of solution pH after equilibrated with $pCO_2$ by:

$$\log(A_T+[H^+]_{eq})=\log[HCO_3^-]=\log(K_1'(K_0)_i(fCO_2))+pH \quad (7)$$

The pH of the LCW's internal solution is measured with a sulfonephthalein indicator. In one embodiment, the sulfonephthalein indicator used for $A_T$ measurements is bromocresol purple (BCP). This indicator has been used for laboratory measurements of seawater alkalinity with a precision better than ±1 μmol kg$^{-1}$. The absorbance characteristics and dissociation behavior of BCP has been measured in both freshwater and seawater media. With an indicator $pK_I$ near 5.8 in seawater media, BCP is ideally suited for pH measurements between 5 and 6.

It is known that solution pH can be calculated from absorbance ratios ($R=_{\lambda_2}A/_{\lambda_1}A$) with the following equation:

$$pH=pK_I+\log((R-e_1)/(e_2-Re_3)) \quad (8)$$

where $K_I$ is the indicator dissociation constant ($K_I=[H^+][I^{2-}]/[HI^-]$) and $pK_I=-\log K_I$. Absorption maxima of $HI^-$ and $I^{2-}$ for bromocresol purple (BCP) are $\lambda_1=432$ nm and $\lambda_2=589$ nm. The symbols $e_1$, $e_2$ and $e_3$ in Eq. (6) refer to indicator molar absorbance ratios at wavelengths $\lambda_1$ and $\lambda_2$ $$e_1={}_{589}\epsilon_{HI}/{}_{432}\epsilon_{HI}, e_2={}_{589}\epsilon_{I}/{}_{432}\epsilon_{HI}, e_3={}_{432}\epsilon_{I}/{}_{432}\epsilon_{HI} \quad (9)$$

where $_\lambda\epsilon_I$ is the molar absorption coefficient of $I^{2-}$ at wavelength $\lambda$ and $_\lambda\epsilon_{HI}$ is the molar absorption coefficient of $HI^-$ at wavelength $\lambda$. Using BCP, the solution pH is given as:

$$pH_T = 5.8182 + 0.00129 + \log((R(25) - 0.00381)/(2.8729 - 0.05104R(25))) \quad (10)$$

$$\text{and } R(25) = R(t)(1 + 0.01869(25 - t)) \quad (11)$$

The fugacity is related to partial pressure of $CO_2$ gas by:

$$fCO_2 = c'pCO_2. \quad (12)$$

Combined equation, $$\log(A_T + [H^+]eq) = \log[HCO_3^-] = \log(K_1'(K_0)_i(pCO_2)/K_I) + E + \log((R(25) - e_1)/(e_2 - R(25)e_3)) \quad (13)$$

where E is conceptually related to activity coefficient of $CO_2$ gas and can be treated as an empirical constant which depends on flow rate and the pressure of the gas; $K_0$ is calculated from the known dependence of Henry's law (gas solubility) constants on temperature and ionic strength. $CO_2$ solubility constants in freshwater and seawater can be expressed as:

$$\ln K_0 = 93.4517(100/T) - 60.2409 + 23.3585 \ln(T/100) + S(0.023517 - 0.023655(T/100) + 0.0047036(T/100)^2) \quad (14)$$

$K_1$ is calculated from the known dependence on temperature and ionic strength based on Roy et al's quantification.

$$\ln(K_1) = -2307.1266/T + 2.83655 - 1.5529413 \ln T + (-4.0484/T - 0.20760841)S1/2 + 0.08468345S - 0.00654208S3/2 + \ln(1 - 0.001005S) \quad (15)$$

In an exemplary embodiment of the invention, bromocresol purple (BCP) sodium salt was obtained from Eastman Kodak Company. Ultrapure grade $Na_2CO_3$ (J. T. Baker) was dried in an 110° C. oven overnight and kept in a desiccator before use. Sodium bicarbonate (Ultra grade, 99.5% minimum) and hydrochloric acid (1N) were obtained from Sigma Chemical.

The absorbance of the indicator dye was measured with Cary 400 spectrophotometer with a fiber optic coupling. The liquid core waveguide (LCW) composed of Teflon AF 2400 tubing was obtained from Biogeneral. Equilibration temperatures were measured using a Model 1521 Hart Scientific thermometer with a calibrated thermistor probe.

With reference again to FIG. 2, in an exemplary embodiment, the main body of the equilibrate chamber 45 is cylindrical with a 2 cm outer diameter (OD) and a 0.5 cm inner diameter (ID). A 15 cm section of LCW 40 is housed in the equilibration chamber 45. The seawater/indicator solution is introduced to the LCW through a T-connector 55 using a peristaltic pump 60. Fiber-optical leads within the LCW extend into the area where solutions are equilibrated. 30% $CO_2$ gas passes through the outside channel 65. Additionally, the gas may be passed through a two meter long copper coil immersed in thermostated water bath prior to entering the outside channel 65. The LCW 40 has an inner volume smaller than 0.1 cm$^3$ whereas the equilibration chamber 45 has a volume on the order of 3 cm$^3$.

In one embodiment, the equilibration cell 50 is housed in a water bath controlled to 0.05° C. Measurements were obtained as follows:

At the beginning of each measurement a reference is taken with seawater without indicator dye.

$CO_2$ (30%) is then passed from the outer chamber after having been thermostated through a long copper coil. In one embodiment, the gas flow rate is monitored with flow meter and controlled to be 15 cm$^3$ per minute.

The LCW is then filled with the sample with indicator added.

The peristaltic pump is then turned off (sealing the sample solution within the LCW) while $CO_2$ gas is constantly flowing outside LCW.

The $pCO_2$ levels across LCW are allowed to equilibrate while absorbances are continuously monitored at 589 nm and 432 nm, as well as a non-absorbing wavelength, 730 nm. These wavelengths are exemplary in nature and other wavelengths are within the scope of the invention.

Eq. (13) can then be used to relate $A_T$ and BCP absorbance ratios.

In determining the calibration constant, "c" for determination of the Eq. (13) standard solution is introduced to the LCW and then following the procedures above, equilibration was achieved. Absorbance ratio measurements were obtained at 589, 432 and 730 nm and the constants in Eq. 13 are calculated based on Eq. 14 and 15. [H+] concentration is calculated based on equilibration R ratio. The constant c is calculated as:

$$E = \log(A_T + [H^+]eq) - \log(K_1'(K_0)_i(pCO_2)/K_I) - \log((R(25) - e_1)/(e_2 - R(25)e_3)) \quad (16)$$

In an exemplary embodiment, a seawater sample collected from 600 m deep is used to demonstrate the application of the present invention for $A_T$ measurement. The salinity of the sample was measured to be 34.750 with a Portsal salinometer. The alkalinity of this seawater sample was measured by LCW technique described above.

Figure 3:
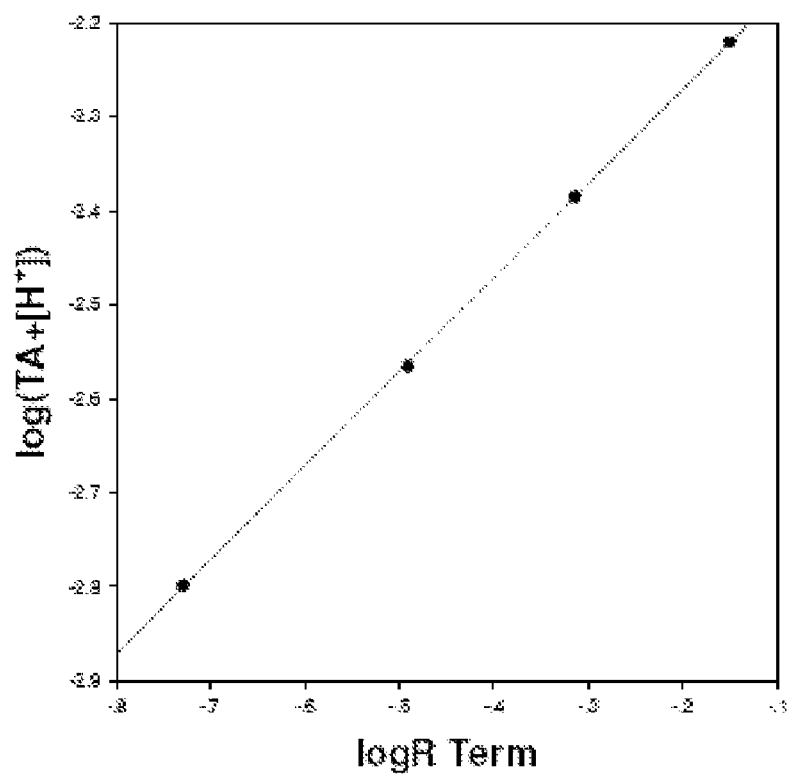
FIG. 3 is an illustration of an $A_T$ measurement obtained using a 0.8 mm OD/ 0.76 mm ID LCW in accordance with an embodiment of the invention.
Figure 4:
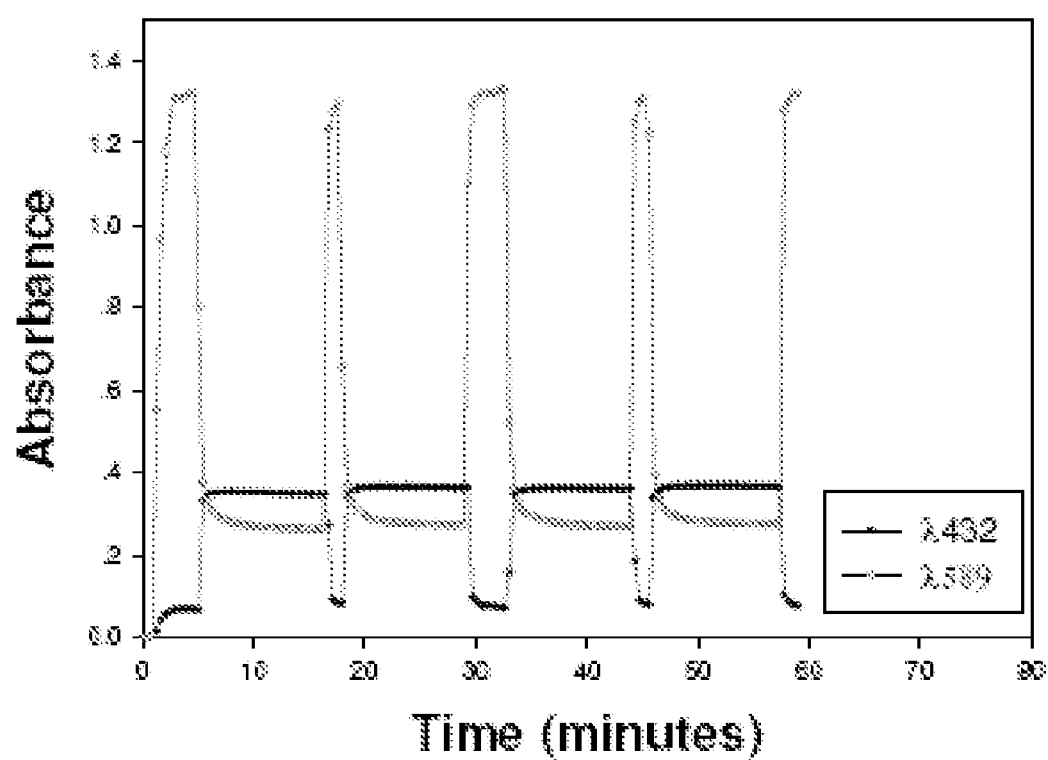
FIG. 4 illustrates the absorbance ratio measurements in accordance with an embodiment of the invention.

FIG. 3 shows the $A_T$ measurement obtained in accordance with the present invention using a 0.8 mm OD/0.76 mm ID LCW. Observations of both $_{589}A$ and $_{432}A$ indicate that 5 min is usually sufficient for system equilibration. Subsequent to system equilibration, FIG. 4 shows that absorbances at each wavelength are quite stable.

The constant E in Eq. 14 is measured with certified reference material (CRM) provided by Dr. Andrew Dickson with known $A_T$ and summarized in the table of FIG. 5. Average of 9 measurements gives E=0.05404. Thus, natural seawater alkalinity can be measured using $$\log(A_T + [H^+]eq) = \log(K_1'(K_0)_i(pCO_2)/K_I) + 0.05404 + \log((R(25) - e_1)/(e_2 - R(25)e_3)) \quad (17)$$

for a wide range of salinity and temperature for the batch of standard prepared.

Spectrophotometric procedures using liquid core waveguides provide simple and robust $A_T$ measurement of natural samples. Spectrophotometric $A_T$ measurements are field portable and are easily adapted to in-situ analysis. The time required for system equilibration is influenced somewhat by temperature but is generally less than 10 minutes. Compared with equilibration time in total $CO_2$ measurement where acidified seawater sample is passed through outside chamber of LCW, the equilibration time is dramatically reduced when $CO_2$ gas is used as equilibration gas. The response of the inner sample pH to the diffusion is almost instantaneous when the sample flow is stopped and the equilibration process is initiated. Most of the kinetic process completes in first two minutes. Tests show that when thin wall and small diameter LCW is used, the equilibration time could be shortened even further.

In a particular embodiment of the invention, 30% $CO_2$ was chosen as equilibration gas. Such concentration is chosen so that for seawater $A_T$ analyses, the absorbance ratio of acid and base form of the indicator are close to one at normal seawater $A_T$ and over wide range of $A_T$ values the pH of the equilibrated sample is well within the indicating range of BCP.

FIG. 3 demonstrates that over wide $A_T$ range, the pH changes in the seawater sample are proportional to the $A_T$ levels and thus just one standard gas allow wide range of $A_T$ to be measured. It is noticed that Eq. 16 is only applicable to 0.7 m NaCl solution. For seawater analyses Eq. 17 is used. Similar to the pH measurement, when $pCO_2$ level is fixed the calibration constant c should be constant at fixed temperature and salinity and not instrument dependent.

As an alternative to $CO_2$ gas as equilibration phase, a $NaHCO_3$ solution could be used to provide the equilibration gaseous phase upon acidification.

The precision of $A_T$ measurements depends principally on the precision of instrumental absorbance ratio measurements. Variations in R on the order of 0.001 correspond to variations in $A_T$ on the order of 0.1%.

REFERENCES

G. M. Robert-Baldo, J. Morris R. H. Byrne, Ana. Chem. 57 (1985) 2564

R. H. Byrne, J. A. Breland, Deep-sea research. Part A 36 (1989) 803.

T. D. Clayton, R. H. Byrne, Deep-sea research. Part A 40 (1993) 2115.

S. McElligott, R. H. Byrne, R. A. Feely, Marine Chemistry 60 (1998) 63.

R. H. Byrne, S. McElligott, F. J. Millero, Deep-sea research. Part A, 46 (1999) 1985.

R. H. Byrne Anal. Chem. 59 (1987) 1479

M. D. DeGrandpre, M. M. Baehr, T. R. Hammar, Anal. Chem. 71 (1999) 1152.

R. D. Waterbury, W. Yao, R. H. Byrne, Analytica chimica acta. 357 (1997) 99

E. Kaltenbacker, E. T. Steimle, R. H. Byrne, Underwater Technology, Proceedings of the 2000 International Symposium, (2000) 41.

A. Yu Alentiev, Yu. P. Yampolskii, V. P. Shantarovich, S. M. Nemser, N. A. Plate, J. Membrane Sci. 126 (1997) 123.

I. Pinnay, L. G. Toy, J. Membrane Sci. 109, (1996) 125.

W. Yao, R. H. Byrne, Deep-sea research. Part A 45 (1998) 1383

W. Yao, R. H. Byrne, Environ. Sci. Technol. 35 (2001) 1197.

H. Zhang, R. H. Byrne, Mar. Chem. 52 (1996) 17.

R. F. Weiss, Mar. Chem. 2 (1974) 203.

F. J. Millero, Geochim. Cosmochim. Acta, 59 (1995) 661

The disclosure of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of measuring the total alkalinity of a sample liquid using a liquid core waveguide having a gas permeable membrane, the liquid core waveguide positioned in an interior cavity of an equilibration chamber, the method comprising the steps of:
   introducing a flow of gas into the interior cavity of the equilibration chamber, the interior cavity of the equilibration chamber surrounding the liquid core waveguide;
   introducing a sample liquid including a pH indicator into an interior of the liquid core waveguide;
   allowing the gas to equilibrate across the gas permeable membrane of the liquid core waveguide;
   measuring the absorbance ratio of the sample liquid at a plurality of wavelengths using the liquid core waveguide, after the gas has equilibrated across the gas permeable membrane of the liquid core waveguide; and
   calculating the total alkalinity of the sample liquid from the measured absorbance ratios.

2. The method of claim 1, wherein the total alkalinity ($A_T$) is calculated according to the equation:

$$\log(A_T + [H^+]) = \log(K_1'(K_0)_i(pCO_2)/K_1) + E + \log((R(25) - e_1)/(e_2 - R(25)e_3)) \text{ where;}$$

$[H^+] = 10^{-pH}$, $K_0$ is the Henry's law constant, $K_1'$ is the dissociation constant of carbonic acid, the subscript i refers to the sample liquid within the waveguide, E is an empirical derived constant, $K_1$ is an indicator dye dissociation constant, $R(25)$ is a ratio of the pH indicator absorbance at 589 and 432 nm, and $e_1$ and $e_2$ and $e_3$ are molar absorptivity ratios appropriate to the pH indicator.

3. The method of claim 1, wherein the pH indicator is a sulfonephthalein pH indicator.

4. The method of claim 1, wherein the pH indicator is bromocresol purple.

5. The method of claim 1, further comprising the step of passing the flow of gas though a thermostated water bath prior to introducing the flow of gas into the interior cavity of the equilibration chamber.

6. The method of claim 1, further comprising the step of housing the equilibration chamber in a thermostated water bath.

7. The method of claim 1, further comprising the step of measuring the absorbance ratio of the liquid sample without the pH indicator to establish a reference.

8. The method of claim 1, wherein the flow of gas is introduced at a controlled rate.

9. The method of claim 1, further comprising the step of sealing the interior of the liquid core waveguide after the sample liquid has been introduced.

10. The method of claim 1, wherein the gas is selected from the group consisting of $CO_2$, $NaHCO_3$ and 30% $CO_2$.

11. A system for measuring the total alkalinity of a sample liquid, the system comprising:
   a equilibration chamber having an interior cavity;
   a liquid core waveguide having a gas permeable membrane, the liquid core waveguide positioned within the interior cavity of the equilibration chamber, the liquid core waveguide for measuring the absorbance ratio of the sample liquid at a plurality of wavelengths;
   a gas flow introduced into the interior cavity of the equilibration chamber;
   a sample liquid including a pH indicator introduced into the interior of the liquid core waveguide; and
   means for calculating the total alkalinity of the sample liquid from the measured absorbance ratios.

12. The system of claim 11, wherein the total alkalinity ($A_T$) calculated according to the equation:

$$\log(A_T + [H^+]) = \log(K_1'(K_0)_i(pCO_2)/K_1) + E + \log((R(25) - e_1)/(e_2 - R(25)e_3)) \text{ where;}$$

$[H^+]=10^{-pH}$, $K_0$ is the Henry's law constant, $K_1'$ is the dissociation constant of carbonic acid, the subscript i refers to the sample liquid within the waveguide, E is an empirical derived constant, $K_1$ is an indicator dye dissociation constant, R(25) is a ratio of the pH indicator absorbance at 589 and 432 nm, and $e_1$ and $e_2$ and $e_3$ are molar absorptivity ratios appropriate to the pH indicator.

13. The system of claim 11, wherein the pH indicator is a sulfonephthalein pH indicator.

14. The system of claim 11, wherein the pH indicator is bromocresol purple.

15. The system of claim 11, further comprising a thermostated water bath positioned between the gas flow and the interior cavity of the equilibration chamber.

16. The system of claim 11, further comprising a flow controller for controlling the flow rate of the gas.

17. The system of claim 11, wherein the interior of the liquid core waveguide is sealable.

18. The system of claim 11, wherein the gas is selected from the group consisting of $CO_2$, $NaHCO_3$ and 30% $CO_2$.

* * * * *